(12) United States Patent
Patzke

(10) Patent No.: US 9,766,234 B2
(45) Date of Patent: *Sep. 19, 2017

(54) SCREENING PROCESS FOR FINDING SAMPLES HAVING A FUNCTIONALITY DISORDER OF THE GPIB-VON WILLEBRAND FACTOR INTERACTION

(71) Applicant: Siemens Healthcare Diagnostics Products GmbH, Marburg (DE)

(72) Inventor: Juergen Patzke, Marburg (DE)

(73) Assignee: SIEMENS HEALTHCARE DIAGNOSTICS PRODUCTS GMBH, Marburg (DE)

( * ) Notice: Subject to any disclaimer, the term of this patent is extended or adjusted under 35 U.S.C. 154(b) by 516 days.

This patent is subject to a terminal disclaimer.

(21) Appl. No.: 13/779,904

(22) Filed: Feb. 28, 2013

(65) Prior Publication Data
US 2013/0230868 A1 Sep. 5, 2013

(30) Foreign Application Priority Data
Mar. 5, 2012 (EP) .................................. 12158022

(51) Int. Cl.
*G01N 33/566* (2006.01)
*G01N 33/86* (2006.01)

(52) U.S. Cl.
CPC ........... *G01N 33/566* (2013.01); *G01N 33/86* (2013.01); *G01N 2333/755* (2013.01)

(58) Field of Classification Search
CPC . G01N 33/566; G01N 33/86; G01N 2333/755
See application file for complete search history.

(56) References Cited

U.S. PATENT DOCUMENTS

| | | | | |
|---|---|---|---|---|
| 7,608,695 B2 | 10/2009 | Fukuchi et al. | ......... | 530/388.25 |
| 2010/0136589 A1 | 6/2010 | Althaus | | |

FOREIGN PATENT DOCUMENTS

| EP | 1850133 | 10/2007 |
|---|---|---|
| EP | 12158022 | 7/2012 |
| WO | WO 0102853 | 1/2001 |
| WO | WO 2009007051 | 1/2009 |
| WO | WO 2009026551 | 2/2009 |

OTHER PUBLICATIONS

Anderson, The Clinical Plasma Proteome: A Survey of Clinical Assays for Proteins in Plasma and Serum, Clinical Chemistry, 56:2, 177-185 (2010).*
Federici, A.B. et al., A sensitive ristocetin co-factor activity assay with recombinant glycoprotein IBa for the diagnosis of patients with low von Willebrand factor levels, Haematologica 89(1): 77-85, (2004).
Lopez, J.A. et al., Cloning of the alpha chain of human platelet glycoprotein Ib: a transmembrane protein with homology to leucine-rich alpha2-glycoprotein, Proc. Natl. Acad. Sci., 84: 5615-5619, (1987).
Vanhoorelbeke, K. et al., A reliable von Willebrand Factor: Ristocetin cofactor enzyme-linked immunosorbent assay to differentiate between type 1 and type 2 von willebrand disease, Seminars in Thrombosis and Hemostasis, 28(2): 161-165, (2002).
Beer, J.H. et al., Glycocalicin: A New Assay—The Normal Plasma Levels and Its Potential Usefulness in Selected Diseases, Blood, 83(3): 691-702, (1994).
Firbas, C. et al., Targeting von Willebrand factor and platelet glycoprotein Ib receptor, Expert Rev. Cardiovasc. Ther., 8(12): 1689-1701, (2010).
Hayata, K. et al., A new binding assay of von Willebrand factor and glycprotein Ib using solid-phase biotinylated platelets, J Pharmacol Sci, 108: 217-221, (2008).
Matsubara, Y. et al., Identification of a novel point mutation in platelet glycoprotein Iba, Gly to Ser at residue 233, in a Japanese family with platelet-type von Willebrand disease, Journal of Thrombosis and Haemostasis, 1: 2198-2205, (2003).
Vanhoorelbeke, Karen et al., A reliable and Reproducible ELISA Method to Measure Ristocetin Cofactor Activity of von Willebrand Factor, Thrombosis and Haemostasis, 83(1.1): 107-113, (2000).

* cited by examiner

Primary Examiner — Andrea S Grossman
(74) Attorney, Agent, or Firm — Slayden Grubert Beard PLLC

(57) ABSTRACT

The invention relates to a screening process for determining a disordered von Willebrand factor (VWF)-GPIb interaction in a patient's sample. This comprises contacting the sample with isolated GPIb.alpha. protein, with VWF protein and with a solid phase associated with an antibody specific for said isolated GPIb.alpha. protein, and determining complex formation.

14 Claims, 1 Drawing Sheet

SCREENING PROCESS FOR FINDING SAMPLES HAVING A FUNCTIONALITY DISORDER OF THE GPIB-VON WILLEBRAND FACTOR INTERACTION

This application incorporates by reference the sequence listing which is submitted together with this application in computer readable form which has the file name 2011P27081US_ST25.txt and is 7 kb.

CROSS-REFERENCE TO RELATED APPLICATIONS

This application claims the benefit of European Patent Application No. 12158022 filed on Mar. 5, 2012, the disclosure of which is incorporated, in its entirety, by this reference.

TECHNICAL FIELD

The present invention is in the field of coagulation diagnostics and relates to a screening process for determining a disordered von Willebrand factor (VWF) and/or GPIb interaction in a sample.

BACKGROUND

Von Willebrand factor (VWF) is a high molecular weight, multimeric glycoprotein in blood plasma, which has important functions in the process of primary hemostasis. VWF possesses, inter alia, binding sites for collagen and for glycoprotein Ib (GPIb) which is located on the surface of platelets. GPIb is an integral membrane protein which, together with another integral membrane protein, glycoprotein IX (GPIX), forms the glycoprotein Ib-IX-receptor complex in the platelet membrane. GPIb is a two-chain molecule comprising a heavy chain with an apparent molecular mass of about 145 kDa (synonym: alpha chain or GPIb.alpha.) and a light chain with an apparent molecular mass of about 22 kDa (synonym: beta chain or GPIb.beta.), which are connected to one another by disulfide bonds (Lopez, J. A. et al., Cloning of the .alpha. chain of human platelet glycoprotein Ib: A transmembrane protein with homology to leucine-rich .alpha..sub.2-glycoprotein. Proc. Natl. Acad. Sci. USA 1987, 84: 5615-5619). Glycocalicin is a fragment of the GPIb.alpha. chain, which is proteolytically removed from the intact receptor in the platelet membrane. Glycocalicin is detectable in plasma. Increased plasma concentrations of free glycocalicin indicate a disorder of platelet function (Beer, J. H. et al., Glycocalicin: A New Assay—The Normal Plasma Levels And Its Potential Usefulness in Selected Diseases. Blood 1994, 83(3): 691-702).

In the case of vascular injury, collagen surfaces are exposed to which VWF binds. Due to its binding to collagen and under the influence of increased shear forces acting on the collagen-bound VWF, VWF is altered or activated in such a way that it can bind to the amino-terminal end of the GPIb heavy chain (GPIb.alpha.) in the GPIb-IX-receptor complex of the platelet membrane. In this way, the activated VWF captures passing platelets, resulting in the formation of a first agglomerate of VWF, collagen and platelets at the site of the injury. Subsequently, the platelets are activated, thereby also starting plasmatic coagulation which finally, after multiple amplifying cascades and attachment of further platelets, results in the wound being closed. VWF-GPIb interaction disorders increase hemorrhagic tendencies.

Qualitative or quantitative VWF disorders cause what is known as a von Willebrand syndrome (synonym: von Willebrand disease, VWD), one of the most common inheritable hemorrhagic conditions. Various screening processes are available for diagnosing a von Willebrand syndrome, for example bleeding time (BT) determination, quantitative processes for determining the concentration of VWF antigen (VWF:Ag), such as ELISA assays for example, and processes for determining VWF activity, such as ristocetin-induced platelet agglutination (VWF:RCo).

The newest generation of functional assays for determining VWF activity involves determining the ability of VWF to bind GPIb.alpha.

Assays have been disclosed which comprise using wild-type GPIb.alpha. and determining VWF binding to GPIb.alpha. in the presence of ristocetin (WO 01/02853 A2; Vanhoorelbeke, K. et al., A reliable von Willebrand factor: Ristocetin cofactor enzyme-linked immunosorbent assay to differentiate between type 1 and type 2 von Willebrand disease. Semin Thromb Hemost. 2002, 28(2): 161-165; Federici, A. B. et al., A sensitive ristocetin co-factor activity assay with recombinant glycoprotein Ib.alpha. for the diagnosis of patients with low von Willebrand factor levels. Haematologica 2004, 89(1): 77-85).

Other assays have been disclosed which make use of GPIb.alpha. "gain-of-function" mutations which are known to have a higher affinity for VWF and interact with VWF more strongly than wild-type GPIb.alpha. protein. These assays enable VWF binding to the mutated GPIb.alpha. to be determined in the absence of ristocetin (WO 2009/007051 A2 or WO 2009/026551 A1).

Defects of the GPIb protein likewise cause hemorrhagic conditions. Gain-of-function mutations of the GPIb protein are the cause of platelet-type von Willebrand syndrome (PT-VWD), an autosomally dominantly transmitted hemorrhagic condition. Substitution of the methionine residue in position 239 of the GPIb.alpha. chain by a valine residue (M239V) has been described by Russell & Roth (Russell, S. D. & Roth, G. J., Pseudo-von Willebrand Disease: A mutation in the platelet glycoprotein Ib.alpha. gene associated with a hyperactive surface receptor. Blood 1993, 81(7): 1787-1791). Mutations in position 233 of the GPIb.alpha. chain may also cause PT-VWD (Matsubara, Y. et al., Identification of a novel point mutation in platelet glycoprotein Ib.alpha., Gly to Ser at residue 233, in a Japanese family with platelet-type von Willebrand disease. Journal of Thrombosis and Haemostasis 2003, 1: 2198-2205).

If a patient is diagnosed with an increased tendency toward hemorrhage, the cause of the disorder must be detected in order to be able to initiate a suitable therapy. Owing to the multiplicity of possible disorders which may cause an increased tendency toward hemorrhage, the availability of screening assays that firstly enable the functionality of certain parts of the coagulation system to be investigated is desirable in clinical diagnostics. If a disorder can be located in a certain part with the aid of such a screening assay, specific individual assays may be carried out in order to specify the exact cause. If no disorder is found in a certain part with the aid of a screening assay, specific individual assays need not be carried out.

The object addressed by the present invention was therefore that of providing a screening process which enables VWF-GPIb interaction disorders to be detected. Such a process should be equally sensitive to VWF disorders and GPIb protein disorders.

VWF-GPIb interaction disorders may be caused, for example, by a) quantitative or qualitative disorders of the VWF protein, such as, for example, states of abnormal deficiency, absence of the large multimers, lack of factor VIII binding ability;

b) VWF inhibitors such as, for example, autoantibodies against VWF which prevent VWF from binding to GPIb, or increased plasma concentrations of glycocalicin which occupies the VWF binding sites and thus diminishes VWF activity, or VWF-inhibiting therapeutic drugs such as, for example, ARC1779, a VWF-binding aptamer, or AJW200, a humanized monoclonal anti-VWF antibody (Firbas, C. et al., Targeting von Willebrand factor and platelet glycoprotein Ib receptor. Expert Rev. Cardiovasc. Ther. 2010, 8 (12): 1689-1701), or GPIb fragment employed as a therapeutic drug (Hennan, J. K. et al., Pharmacologic inhibition of platelet vWF-GPIb.alpha. interaction prevents coronary artery thrombosis. Thromb Haemost 2006, 95: 469-75);

c) VWF activators;

d) qualitative disorders of the GPIb protein, such as, for example, gain-of-function mutations having a higher affinity for VWF and therefore accelerating VWF breakdown;

e) GPIb inhibitors such as, for example, autoantibodies against GPIb which prevent VWF from binding to GPIb, or therapeutic drugs such as H6B4-Fab for example, the Fab fragment of a humanized monoclonal anti-GPIb.alpha. antibody (see likewise Firbas, C. et al.);

f) GPIb activators (e.g. thrombin).

The object is achieved by contacting the sample from a patient with isolated GPIb.alpha. protein, with VWF protein and with a solid phase associated with a GPIb.alpha.-specific antibody, and determining formation of a complex between VWF protein, GPIb.alpha. protein and the solid phase. VWF-GPIb interaction is disordered if said complex formation is reduced or increased compared to normal. Such samples should then be tested specifically for VWF and GPIb disorders with the aid of specific individual assays.

SUMMARY

The present invention therefore relates to a process for finding a sample having a disordered VWF-GPIb interaction, comprising a. contacting the sample with GPIb.alpha. protein, with VWF protein and with a solid phase associated with an antibody specific for said isolated GPIb.alpha. protein, and b. determining formation of a complex between VWF protein, GPIb.alpha. protein and the solid phase.

Said process detects VWF-GPIb interaction disorders both on the VWF side and on the GPIb side.

The term "sample" comprises biological fluids, particularly from humans and animals, such as blood, plasma or serum.

The GPIb.alpha. protein used in the process of the invention may be a recombinantly or synthetically produced GPIb.alpha. protein. Known prokaryotic or eukaryotic expression systems such as, for example, expression in bacteria (e.g. E. coli), in yeasts (e.g. Saccharomyces cerevisiae, Pichia pastoris), in plant, animal or human cell cultures, are suitable for producing recombinant GPIb.alpha. protein. Known in vitro protein synthesis techniques are suitable for producing synthetic GPIb.alpha. protein, such as, for example, solid phase syntheses (e.g. Merrifield synthesis). The GPIb.alpha. protein used in the process of the invention is preferably recombinantly produced GPIb.alpha. protein produced in a culture of human cells, preferably in a culture of human embryonic kidney cells (HEK cells).

Preference is given to adding GPIb.alpha. protein to the assay mix in an amount such that a final concentration of less than 1.4 pg/ml GPIb.alpha. in the assay mix, particularly preferably of less than 0.7.mu.g/ml GPIb.alpha. in the assay mix, is obtained.

The GPIb.alpha. protein used in the process of the invention may be fused at the N terminus to the homologous human GPIb.alpha. signal sequence, MPLLLLLLLL-PSPLHP (SEQ ID NO: 2, also referred to as amino acid residues −16 to −1). Alternatively, the GPIb.alpha. protein used may be fused at the N terminus to a heterologous signal sequence, i.e. to a polypeptide which is not normally present in the human GPIb.alpha. polypeptide, but which has a beneficial influence on expression and/or secretion of the recombinantly expressed GPIb.alpha. protein in the chosen expression system. An example of a suitable heterologous signal sequence is MPLQLLLLLILLGPGNSLQLWDT-WADEAEKALGPLLARDRR (SEQ ID NO: 3).

The GPIb.alpha. protein used in the process of the invention may furthermore be fused at the C terminus to one or more affinity tags which enable the, for example recombinantly expressed, protein to bind to an affinity carrier, thereby enabling recombinantly expressed GPIb.alpha. protein to be purified, for example. Preference is given to small affinity tags of no more than 12 amino acids in length. Particular preference is given to affinity tags from the group consisting of His tag, Flag tag, Arg tag, c-Myc tag, and Strep tag. Examples of suitable affinity carriers that bind with high affinity to an affinity tag are specific antibodies, immobilized cations (e.g. Ni.sup.2+ with affinity for His tags) or other types of binding partners (e.g. streptavidin with affinity for Strep tags).

In one embodiment of the process of the invention, the isolated GPIb.alpha. protein is human wild-type GPIb.alpha. protein (SEQ ID NO: 1) or a functional fragment thereof. When using human wild-type GPIb.alpha. protein or a functional fragment thereof, ristocetin, botrocetin or a ristocetin equivalent is furthermore added to the assay mix in order to induce in vitro binding of dissolved VWF to the wild-type GPIb.alpha. protein or fragments thereof.

In another embodiment, the isolated GPIb.alpha.protein has been mutated and—compared to the wild-type sequence of human GPIb.alpha. protein (SEQ ID NO: 1)—contains at least the amino acid residues 1-268 and at least one Xaa substitution in each of at least two of positions 233, 235 and 239. The Xaa substitutions of the glycine residue in position 233 and of the methionine residue in position 239 of the GPIb.alpha. chain preferably comprise a valine residue (G233V and M239V, respectively) or a serine residue (G233S and M239S, respectively). There can be any combination of the different Xaa substitutions in the two positions. Particular preference is given to the G233V/M239V combination. The Xaa substitution Xaa of the aspartic acid residue in position 235 preferably comprises a tyrosine residue (D235Y). The mutations mentioned are gain-of-function mutations which have a significantly higher affinity for VWF and interact with VWF more strongly than wild-type GPIb.alpha. protein. When using this kind of mutation, neither ristocetin nor botrocetin or a ristocetin equivalent is added to the assay mix.

The VWF protein used in the process of the invention may be isolated high molecular weight, multimeric VWF. Human VWF monomer is synthesized in vivo initially by way of a 2813 amino acid precursor protein. Intracellular processing produces VWF multimers which may grow to more than 20,000 kDa. These multimers consist of 275 kDa VWF monomers of 2,050 amino acids in length, which are arranged in a linear fashion and linked to one another via disulfide bonds. VWF circulates in the plasma in the form of globular multimers of different sizes from about 500 kDa (dimer) to over 15,000 kDa. The isolated VWF protein used in the process of the invention may either be obtained from donor plasmas or be recombinantly expressed with the aid of processes known to a person skilled in the art. Alternatively, the VWF protein may also be added to the assay mix in a natural form, for example by way of a normal plasma.

Preference is given to adding VWF protein to the assay mix in an amount such that a final concentration of 0.1-20% of the norm VWF in the assay mix, particularly preferably of 0.5-10% of the norm in the assay mix, is obtained.

The antibody specific for the isolated GPIb.alpha. protein, which is used in the process of the invention, may be any antibody that specifically recognizes the GPIb.alpha. protein used in the assay mix. Antibodies which are suitable in principle are GPIb.alpha. antibodies binding to an epitope of the GPIb.alpha. protein. If a recombinant GPIb.alpha. protein fused to an affinity tag is used, an affinity tag-specific antibody that specifically binds to said affinity tag is also suitable. The term antibody also includes antibody fragments having the same antigen specificity as the complete antibody.

The antibody is associated with a solid phase. The term "associated" has a broad meaning and comprises, for example, covalent and noncovalent binding, direct and indirect binding, adsorption to a surface and inclusion in a depression. In covalent binding, the antibody is bound via a chemical bond to the solid phase. An example of noncovalent binding is surface adsorption. In addition to direct binding to the solid phase, the antibody may also be bound indirectly to the solid phase via specific interaction with other specific binding partners, for example via specific interaction with another antibody.

The term "solid phase" for the purposes of the present invention comprises an object which consists of porous and/or nonporous, water-insoluble material and which may have very different shapes, such as, for example, vessel, tube, microtiter plate (ELISA plate), bead, microparticle, rod, strip, filter paper or chromatographic paper, etc. The surface of the solid phase is normally hydrophilic or can be made hydrophilic. The solid phase may consist of very different materials such as, for example, inorganic and/or organic materials, synthetic materials, naturally occurring and/or modified naturally occurring materials. Examples of solid phase materials are polymers such as, for example, cellulose, nitrocellulose, cellulose acetate, polyvinyl chloride, polyacrylamide, crosslinked dextran molecules, agarose, polystyrene, polyethylene, polypropylene, polymethacrylate or nylon; latex; ceramics; glass; metals, in particular precious metals such as gold and silver; magnetite; mixtures or combinations thereof.

The solid phase may have a coating of one or more layers, for example of proteins, carbohydrates, lipophilic substances, biopolymers, organic polymers or mixtures thereof, for example for suppressing or preventing unspecific binding of sample components to the solid phase, or for example for improving the suspension stability of particulate solid phases, the storage stability, the design stability or the resistance to UV light, microbes or other destructive agents.

Contacting isolated GPIb.alpha. protein with VWF protein and with a solid phase associated with an antibody specific for said isolated GPIb.alpha. protein results in the formation of a complex composed of said three components. An altered complex formation compared to the normal one is measured if the patient's sample contains substances that influence said complex formation, for example GPIb inhibitors or VWF inhibitors or activators or glycocalicin, or if the sample contains functionally disordered GPIb or VWF proteins that compete with the functional added proteins during said complex formation.

In a preferred embodiment of the process of the invention, the antibody specific for the isolated GPIb.alpha. protein is associated with a particulate solid phase, preferably with latex particles. In this case, formation of the complex between VWF protein, GPIb.alpha. protein and the solid phase may be determined by measuring agglutination of said particulate solid phase. The agglutination reaction which correlates with said complex formation and consequently with the GPIb and VWF activities in the sample may be determined quantitatively, for example, by utilizing the light scatter on the particle aggregates by way of measuring the intensity of the scattered light (nephelometry) or by way of measuring the turbidity of the medium (turbidimetry).

In another embodiment of the process of the invention, the antibody specific for the isolated GPIb.alpha. protein is associated with a non-particulate solid phase, preferably with the surface of a microtiter plate. In this case, formation of the complex between VWF protein, GPIb.alpha. protein and the solid phase may be determined by measuring the amount of VWF bound via the complex to the solid phase. The amount of VWF bound via the complex to the solid phase may be determined, for example, by using an anti-VWF antibody which is associated directly or indirectly with a component of a signal-producing system and which therefore allows the amount of VWF bound to be quantified.

The present invention also relates to a test kit for carrying out a process of the invention, comprising a first reagent containing isolated GPIb.alpha. protein, a second reagent containing VWF protein, and a third reagent containing a solid phase, preferably a particulate solid phase, which is associated with an antibody specific for said isolated GPIb.alpha. protein.

In one embodiment, the first reagent contains human wild-type GPIb.alpha. protein or a functional fragment thereof. In another embodiment, the first reagent contains a mutated GPIb.alpha. protein which, compared to the wild-type sequence of human GPIb.alpha. protein (SEQ ID NO: 1), contains at least the amino acid residues 1-268 and has an Xaa substitution in each of at least two of positions 233, 235 and 239.

The test kit may further comprise a fourth reagent containing ristocetin or botrocetin.

The test kit may further comprise a fifth reagent containing an anti-VWF antibody.

The reagents may be provided in a liquid or lyophilized form. If a reagent is a lyophilizate, the test kit may in addition contain solvent required for suspending said lyophilizate, such as distilled water or a suitable buffer for example.

In another embodiment, normalization may be performed for improved standardization of the results. For this purpose, the result for the sample is divided by the result for a normal plasma. Thus, a particularly strong VWF-GPIb interaction is expressed by a ratio of greater than 1, and a reduced VWF-GPIb interaction is expressed by a ratio of less than 1. Furthermore, it is also possible to carry out a calibration using a calibrator, said calibrator containing von Willebrand factor. However, the results must be expressed in artificial units, since GPIb-VWF interaction is detected in the sample. An inhibitor of GPIb lowers the results of the assay, although VWF activity remains at a normal level.

Once a sample with disordered VWF-GPIb interaction has been identified with the aid of the process of the invention, subsequent assays should be carried out to define the disorder more closely. This may involve carrying out a variant of the process of the invention, which comprises adding a large excess of either GPIb.alpha. or VWF or both to the assay mix. If a large excess of GPIb.alpha. is added, the assay will respond merely to VWF activity disorders. If a large excess of VWF is added, the assay will respond merely to disorders on the GPIb side of the interaction. If a large excess of both GPIb.alpha. and VWF is added, it may be possible to detect, for example, autoantibodies against the capture antibody bound to the solid phase that prevent GPIb.alpha. binding.

A possible disorder on the GPIb side is an increase or decrease in glycocalicin concentration in the sample. In the presence of a large excess of VWF, and if other disorders can be ruled out, the process may also be utilized for determining the glycocalicin content of the sample (FIG. 2), which requires calibration using a glycocalicin standard. A large excess of VWF may be obtained, for example, by adding 20.mu.l of a reagent containing 1000 or 2000% VWF activity for the assay mix to contain a VWF activity of 99% or 197% of the norm. A large excess of GPIb.alpha. may be obtained, for example, by adding 13.mu.l of a reagent containing 35.mu.g/ml GPIb.alpha. protein for the assay mix to contain 2.2.mu.g/ml GPIb.alpha. protein.

The present invention therefore also relates to a process for determining the concentration of glycocalicin in a sample, comprising contacting the sample with isolated GPIb.alpha. protein, with VWF protein and with a solid phase associated with an antibody specific for said isolated GPIb.alpha. protein, and determining formation of a complex between VWF protein, GPIb.alpha. protein and the solid phase. Determining the glycocalicin concentration requires VWF protein to be added to the assay mix in an amount such that a VWF activity of at least 50%, preferably of more than 100%, of the norm is obtained in the assay mix. Preference is given to carrying out a calibration using calibrators containing different glycocalicin concentrations.

EXAMPLES

Example 1

Screening Process of the Invention for Finding Samples Containing a Disordered VWF-GPIb Interaction The sample used was human citrated plasma from six different donors. 60.mu.l of sample were mixed with 20.mu.l of plasma containing VWF (91% of norm VWF, control plasma N, Siemens Healthcare Diagnostics Products GmbH, Marburg, Germany), 13.mu.l of a solution containing a recombinant gain-of-function GPIb.alpha. protein fragment (amino acids 1-285 with amino acid substitutions G233V and M239V; 8.4.mu.g/ml) and 70.mu.l of an NaCl buffer and incubated for two minutes. Subsequently, 40.mu.l of a latex particle reagent containing latex particles coated with anti-GPIb.alpha. antibodies were added to the assay mix.

Absorbance at 570 nm of the reaction mixture was measured turbidimetrically. Binding of VWF to GPIb.alpha. and binding of the GPIb.alpha. protein to the latex particles result in particle agglutination. This agglutination leads to an increase in absorbance, the maximum rate of which is determined (mU/min).

Figure 1:
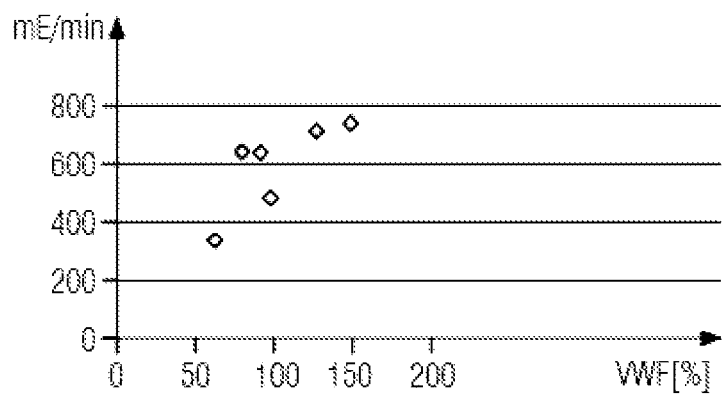
FIG. 1 shows that a latex particle agglutination assay based on the process of the invention is sensitive to different VWF activities.

As FIG. 1 indicates, the process is sensitive to different VWF activities. The rate of agglutination increases with increasing VWF activity in a plasma sample.

In another experiment, various dilutions of a glycocalicin solution rather than donor plasmas were used as samples (0, 1.2, 2.5 and 5.mu.g/ml glycocalicin). The glycocalicin solution was prepared by treating washed platelets with plasmin.

Figure 2:
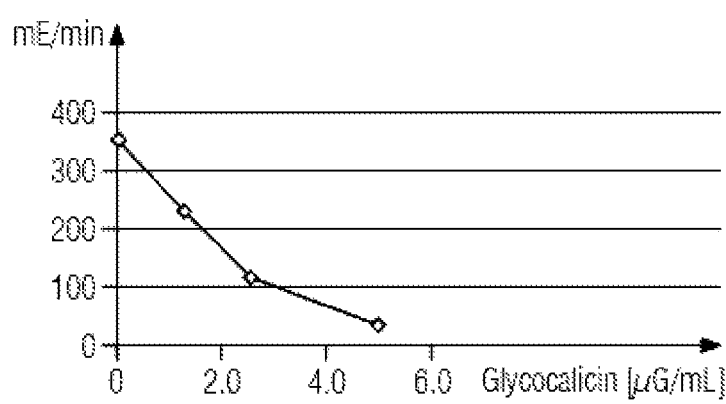
FIG. 2 shows that a latex particle agglutination assay based on the process of the invention is sensitive to different glycocalicin concentrations.

As FIG. 2 indicates, the process is sensitive to different glycocalicin concentrations. The rate of agglutination increases with decreasing glycocalicin concentration in a sample.

In another experiment, a normal plasma pool (control plasma N) rather than donor plasmas was used, which pool had been enriched with different amounts of an anti-GPIb antibody that inhibits GPIb.alpha. binding to VWF (antibody AK2; see Hayata, K. et al., A new binding assay of von Willebrand factor and glycoprotein Ib using solid-phase biotinylated platelets. J Pharmacol Sci 2008, 108: 217-221). Furthermore, citrated plasma with slightly reduced VWF activity from a donor was measured. Table 1 summarizes the results. Accordingly, the process is sensitive to factors that inhibit VWF-GPIb binding. The rate of agglutination decreases with increasing amounts of inhibitor in a sample.

TABLE-US-00001 TABLE 1 Rate of agglutination Sample (mU/min) Normal plasma pool 633 Normal plasma pool+266 10.mu.g/ml AK2 antibody Normal plasma pool+ 133 20.mu.g/ml AK2 antibody Plasma with slightly reduced 348 VWF activity (63.1%)

Example 2

Modification of the Screening Process of the Invention Suitable as a Subsequent Assay As in example 1, human citrated plasma, from five different donors, was used as sample. However, 20.mu.l of a plasma having a VWF activity of 2,000% of the norm due to addition of a VWF concentrate (Hamate, CSL Behring GmbH, Marburg, Germany) rather than VWF-containing normal plasma (91% of norm VWF) were added to the assay mix.

Figure 3:
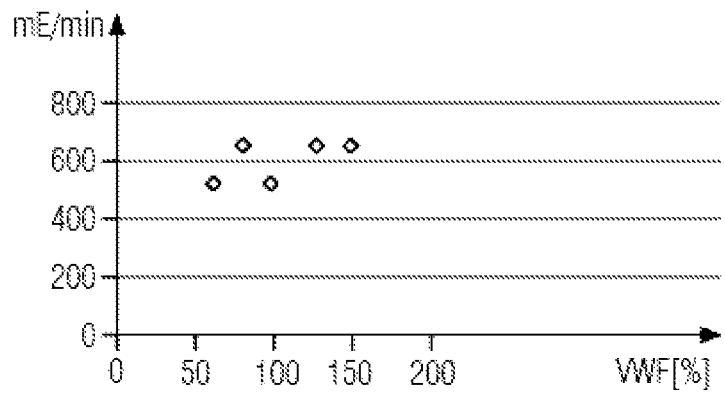
FIG. 3 shows that a latex particle agglutination assay based on the process of the invention is not sensitive to different VWF activities when an excess of VWF has been added to the assay mix.

As FIG. 3 indicates, the process is no longer sensitive to different VWF activities in the donor samples, due to the presence of a large excess of VWF. A process of this kind is sensitive merely to VWF-GPIb interaction disorders on the GPIb side.

The invention claimed is:
1. A method for detecting a sample of biological fluid having a defective von Willebrand factor (VWF)-glycoprotein Ib (GRIb) interaction regardless of whether the defective interaction is caused by a VWF disorder, the method comprising:
   a.) providing an assay mix with a concentration of glycoprotein Ibα (GPIbα) protein of less than 1.4 µg/ml by performing an assay mix process, wherein the assay mix comprises a sample which is not contacted with ristocetin and/or botrocetin, and wherein the assay mix process comprises:
      i.) providing the sample, wherein the sample comprises VWF protein and GPIbα protein; and
      ii.) after providing the sample comprising VWF protein and GPIbα protein:
         a. adding additional GPIbα protein to the sample by contacting the sample with isolated GPIbα protein which has been mutated and, compared to the wild-type sequence of human GPIbα protein, contains at least the amino acid residues 1-268 of SEQ ID NO: 1 and has an amino acid substitution in at least two of positions, wherein the amino acid positions are 233, 235 and 239 of SEQ ID NO: 1;
         b. adding additional VWF protein to the sample by contacting the sample with isolated VWF protein; and
         c. contacting the sample with a particulate solid phase, wherein the particulate solid phase has an antibody specific for said isolated GPIbα protein immobilized thereon;
   b.) measuring the formation of a complex between VWF protein, GPIbα protein and the solid phase in the assay mix, whereby the complex formation involves VWF-GPIb interaction in the assay mix;
   c.) comparing the complex formation in the assay mix with complex formation in a reference sample of the same type of biological fluid as the sample; and
   d.) determining the defective VWF-GPIb interaction, regardless of whether the defective interaction is caused by a VWF disorder, based on a reduced or increased complex formation in the assay mix as compared to the reference sample.

2. The method of claim 1, wherein the mutated GPIbα protein has amino acid substitutions G233V and M239V.

3. The method of claim 1, wherein the assay mix contains less than 0.7 µg/ml GPIbα protein when complex formation is measured.

4. The method of claim 1, further comprising measuring the formation of a complex between VWF protein, GPIbα protein and the solid phase in the assay mix by measuring the VWF protein bound to the solid phase.

5. The method of claim 1, wherein the mutated GPIbα protein has an amino acid substitution selected from the group consisting of G233V, G233S, D235Y, M239V and M239S.

6. The method of claim 1, wherein the mutated GPIbα protein has an amino acid substitution selected from the group consisting of G233S, D235Y, and M239S.

7. The method of claim 1, wherein the assay mix has 0.5%-10% of the normal VWF activity when complex formation is measured.

8. The method of claim 1, wherein the defective VWF-GPIb interaction is caused by (a) quantitative or qualitative disorders of the VWF protein of the sample or (b) the presence of at least one VWF activator or inhibitor in the sample.

9. The method of claim 1, wherein the defective VWF-GPIb interaction is caused by (a) quantitative or qualitative disorders of the GPIbα protein of the sample or (b) the presence of at least one GPIb activator or inhibitor in the sample.

10. The method of claim 1, wherein the assay mix has 0.1-20% of the normal VWF activity when complex formation is measured.

11. The method of claim 10, further comprising measuring the formation of a complex between VWF protein, GPIbα protein and the solid phase in the assay mix by measuring the agglutination of the solid phase.

12. A method for detecting a VWF-GPIb interaction-altering feature in a sample of biological fluid, regardless of whether the defective interaction is caused by a VWF disorder, the method comprising:
   a.) providing an assay mix with a concentration of glycoprotein Ibα (GPIbα) protein of less than 1.4 µg/ml by performing an assay mix process, wherein the assay mix comprises a sample which is not contacted with ristocetin and/or botrocetin, and wherein the assay mix process comprises:
      i.) providing the sample, wherein the sample comprises VWF protein and GPIbα protein; and
      ii.) after providing the sample comprising VWF protein and GPIbα protein:
         a. adding additional GPIbα protein to the sample by contacting the sample with isolated GPIbα protein which has been mutated and, compared to the wild-type sequence of human GPIbα protein, contains at least the amino acid residues 1-268 of SEQ ID NO: 1 and has an amino acid substitution in at least two of positions, wherein the amino acid positions are 233, 235 and 239 of SEQ ID NO: 1;
         b. adding additional VWF protein to the sample by contacting the sample with isolated VWF protein; and
         c. contacting the sample with a particulate solid phase, wherein the particulate solid phase has an antibody specific for said isolated GPIbα protein immobilized thereon;
   b.) measuring the formation of a complex between VWF protein, GPIbα protein and the solid phase in the assay mix, whereby the complex formation involves VWF-GPIb interaction in the assay mix;
   c.) comparing the complex formation in the assay mix with complex formation in a reference sample of the same type of biological fluid as the sample; and
   d.) determining the presence of the VWF-GPIb interaction-altering feature in the sample, regardless of whether the defective interaction is caused by a VWF disorder, based on a reduced or increased complex formation in the assay mix as compared to the reference sample.

13. The method of claim 12, wherein the VWF-GPIb interaction-altering feature includes at least one of (a) quantitative or qualitative disorders of the VWF protein of the sample, or (b) the presence of at least one VWF activator or inhibitor in the sample.

14. The method of claim 12, wherein the VWF-GPIb interaction-altering feature includes at least one of (a) quantitative or qualitative disorders of the GPIbα protein of the sample, or (b) the presence of at least one GPIb activator or inhibitor in the sample.

* * * * *

SEQUENCE LISTING

<160> NUMBER OF SEQ ID NOS: 3

<210> SEQ ID NO 1
<211> LENGTH: 610
<212> TYPE: PRT
<213> ORGANISM: Homo sapiens

<400> SEQUENCE: 1

```
His Pro Ile Cys Glu Val Ser Lys Val Ala Ser His Leu Glu Val Asn
 1               5                  10                  15

Cys Asp Lys Arg Asn Leu Thr Ala Leu Pro Pro Asp Leu Pro Lys Asp
             20                  25                  30

Thr Thr Ile Leu His Leu Ser Glu Asn Leu Leu Tyr Thr Phe Ser Leu
         35                  40                  45

Ala Thr Leu Met Pro Tyr Thr Arg Leu Thr Gln Leu Asn Leu Asp Arg
     50                  55                  60

Cys Glu Leu Thr Lys Leu Gln Val Asp Gly Thr Leu Pro Val Leu Gly
 65                  70                  75                  80

Thr Leu Asp Leu Ser His Asn Gln Leu Gln Ser Leu Pro Leu Leu Gly
                 85                  90                  95

Gln Thr Leu Pro Ala Leu Thr Val Leu Asp Val Ser Phe Asn Arg Leu
            100                 105                 110

Thr Ser Leu Pro Leu Gly Ala Leu Arg Gly Leu Gly Glu Leu Gln Glu
        115                 120                 125

Leu Tyr Leu Lys Gly Asn Glu Leu Lys Thr Leu Pro Pro Gly Leu Leu
    130                 135                 140

Thr Pro Thr Pro Lys Leu Glu Lys Leu Ser Leu Ala Asn Asn Asn Leu
145                 150                 155                 160

Thr Glu Leu Pro Ala Gly Leu Leu Asn Gly Leu Glu Asn Leu Asp Thr
                165                 170                 175

Leu Leu Leu Gln Glu Asn Ser Leu Tyr Thr Ile Pro Lys Gly Phe Phe
            180                 185                 190

Gly Ser His Leu Leu Pro Phe Ala Phe Leu His Gly Asn Pro Trp Leu
        195                 200                 205

Cys Asn Cys Glu Ile Leu Tyr Phe Arg Arg Trp Leu Gln Asp Asn Ala
    210                 215                 220

Glu Asn Val Tyr Val Trp Lys Gln Gly Val Asp Val Lys Ala Met Thr
225                 230                 235                 240

Ser Asn Val Ala Ser Val Gln Cys Asp Asn Ser Asp Lys Phe Pro Val
                245                 250                 255

Tyr Lys Tyr Pro Gly Lys Gly Cys Pro Thr Leu Gly Asp Glu Gly Asp
            260                 265                 270

Thr Asp Leu Tyr Asp Tyr Tyr Pro Glu Glu Asp Thr Glu Gly Asp Lys
        275                 280                 285

Val Arg Ala Thr Arg Thr Val Val Lys Phe Pro Thr Lys Ala His Thr
    290                 295                 300

Thr Pro Trp Gly Leu Phe Tyr Ser Trp Ser Thr Ala Ser Leu Asp Ser
305                 310                 315                 320

Gln Met Pro Ser Ser Leu His Pro Thr Gln Glu Ser Thr Lys Glu Gln
                325                 330                 335

Thr Thr Phe Pro Pro Arg Trp Thr Pro Asn Phe Thr Leu His Met Glu
            340                 345                 350

Ser Ile Thr Phe Ser Lys Thr Pro Lys Ser Thr Thr Glu Pro Thr Pro
        355                 360                 365
```

-continued

Ser Pro Thr Thr Ser Glu Pro Val Pro Glu Pro Ala Pro Asn Met Thr
    370                 375                 380

Thr Leu Glu Pro Thr Pro Ser Pro Thr Thr Pro Glu Pro Thr Ser Glu
385                 390                 395                 400

Pro Ala Pro Ser Pro Thr Thr Pro Glu Pro Thr Pro Ile Pro Thr Ile
                405                 410                 415

Ala Thr Ser Pro Thr Ile Leu Val Ser Ala Thr Ser Leu Ile Thr Pro
            420                 425                 430

Lys Ser Thr Phe Leu Thr Thr Lys Pro Val Ser Leu Leu Glu Ser
        435                 440                 445

Thr Lys Lys Thr Ile Pro Glu Leu Asp Gln Pro Pro Lys Leu Arg Gly
450                 455                 460

Val Leu Gln Gly His Leu Glu Ser Ser Arg Asn Asp Pro Phe Leu His
465                 470                 475                 480

Pro Asp Phe Cys Cys Leu Leu Pro Leu Gly Phe Tyr Val Leu Gly Leu
                485                 490                 495

Phe Trp Leu Leu Phe Ala Ser Val Val Leu Ile Leu Leu Leu Ser Trp
                500                 505                 510

Val Gly His Val Lys Pro Gln Ala Leu Asp Ser Gly Gln Gly Ala Ala
            515                 520                 525

Leu Thr Thr Ala Thr Gln Thr Thr His Leu Glu Leu Gln Arg Gly Arg
530                 535                 540

Gln Val Thr Val Pro Arg Ala Trp Leu Leu Phe Leu Arg Gly Ser Leu
545                 550                 555                 560

Pro Thr Phe Arg Ser Ser Leu Phe Leu Trp Val Arg Pro Asn Gly Arg
                565                 570                 575

Val Gly Pro Leu Val Ala Gly Arg Arg Pro Ser Ala Leu Ser Gln Gly
            580                 585                 590

Arg Gly Gln Asp Leu Leu Ser Thr Val Ser Ile Arg Tyr Ser Gly His
        595                 600                 605

Ser Leu
    610

<210> SEQ ID NO 2
<211> LENGTH: 16
<212> TYPE: PRT
<213> ORGANISM: Homo sapiens

<400> SEQUENCE: 2

Met Pro Leu Leu Leu Leu Leu Leu Leu Pro Ser Pro Leu His Pro
1               5                   10                  15

<210> SEQ ID NO 3
<211> LENGTH: 41
<212> TYPE: PRT
<213> ORGANISM: Artificial
<220> FEATURE:
<223> OTHER INFORMATION: heterologous signal peptide

<400> SEQUENCE: 3

Met Pro Leu Gln Leu Leu Leu Leu Ile Leu Leu Gly Pro Gly Asn
1               5                   10                  15

Ser Leu Gln Leu Trp Asp Thr Trp Ala Asp Glu Ala Glu Lys Ala Leu
                20                  25                  30

Gly Pro Leu Leu Ala Arg Asp Arg Arg
        35                  40